United States Patent [19]

Shinohara

[11] Patent Number: 4,551,140
[45] Date of Patent: Nov. 5, 1985

[54] TUBE FOR MEDICAL INSTRUMENTS AND MEDICAL BAG DEVICE HAVING THE SAME

[75] Inventor: Shuichi Shinohara, Fuji, Japan

[73] Assignee: Terumo Kabushiki Kaisha, Tokyo, Japan

[21] Appl. No.: 426,245

[22] Filed: Sep. 28, 1982

[30] Foreign Application Priority Data

Apr. 1, 1982 [JP] Japan .................................. 57-54714

[51] Int. Cl.$^4$ ................................................ A61M 5/00
[52] U.S. Cl. .................................... 604/262; 138/118; 604/280; 604/408
[58] Field of Search .................... 604/264–267, 604/280–284, 408–410, 54, 262; 138/111, 113–114, 118, 121, 122; 128/207.15

[56] References Cited

U.S. PATENT DOCUMENTS

| | | | |
|---|---|---|---|
| 2,896,619 | 7/1959 | Bellamy | 604/409 |
| 3,419,010 | 12/1968 | Williamson | 604/170 X |
| 3,508,554 | 4/1970 | Sheridan | 604/280 |
| 3,948,273 | 4/1976 | Sanders | 128/207.15 |
| 4,140,162 | 2/1979 | Gajewski et al. | 604/408 X |

OTHER PUBLICATIONS

Firmendruckschrift der Firma Braun Melsungen, "Braun's Blutbeutel", 1965, S. 1 bis 12.

*Primary Examiner*—Dalton L. Truluck
*Attorney, Agent, or Firm*—Frishauf, Holtz, Goodman & Woodward

[57] ABSTRACT

Medical instruments unsuited for gas sterilization, such as blood bag, transfusion bag, blood circuit or the like, are sterilized together with tubes connected thereto by autoclave sterilization. The medical instrument subjected to autoclave sterilization is made of a material such as a resin of vinylchloride group, ethylene-acetate vinyl resin or the like which exhibits a high tendency for blocking. According to the invention, the tubes for medical instruments which are destined for autoclave sterilization are provided on their peripheral surfaces with longitudinal ribs of specific dimensions to diminish the tendency of blocking during the autoclave sterilization and to facilitate the separation of tubes even if any blocking has taken place.

21 Claims, 7 Drawing Figures

FIG.1a
FIG.1b
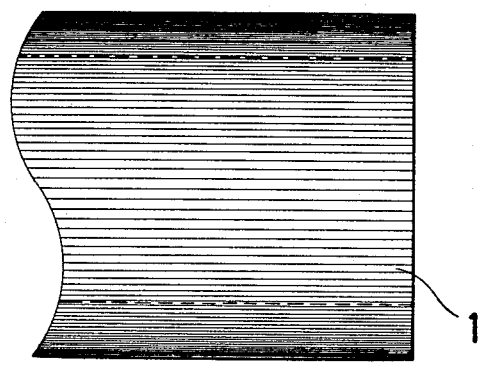
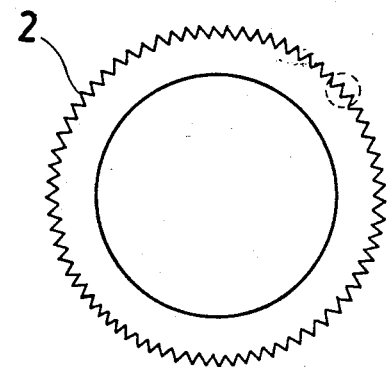
FIG.2c
FIG.2b
FIG.2a
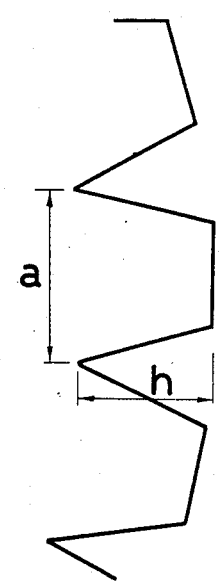
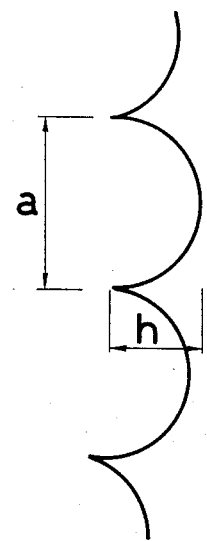
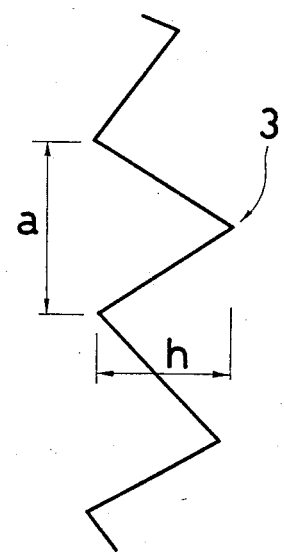

TUBE FOR MEDICAL INSTRUMENTS AND MEDICAL BAG DEVICE HAVING THE SAME

BACKGROUND OF THE INVENTION

1. Field of the Invention

The present invention relates to a tube for medical instruments and, more particularly, to a tube made of a resin which may suffer from blocking during steam autoclave sterilization such as vinychloride resin or EVA resin, etc. and adapted for providing a fluid connection to a medical device intended to be sterilized by steam autoclave and made of a resin of the same kind as above. Such device can be a blood bag, transfusion bag, blood transfusion set, transfusion set, blood circuit and so forth. The present invention relates also to a medical bag device having the above-described tube.

2. Description of the Prior Art

There are some medical instruments or devices which are not suitable for sterilization by gas. Examples of such medical instruments are blood bags, transfusion bags, blood transfusion sets, transfusion sets, blood circuits and so forth. These medical instruments, therefore, are usually sterilized together with tubes connected thereto by an autoclave sterilization. More specifically, the autoclave sterilization is conducted by placing a multiplicity of medical instruments in a sterilization chamber with the tubes bundled or stacked for easier sterilization, and applying steam of a temperature higher than 121° C. In this autoclave sterilization, a problem arises from the fact that the materials of the medical instruments and the tubes are of a resin of vinylchloride group or ethylene-vinylacetate (EVA) group which resin has a large tendency for blocking. Namely, the medical instruments and the tubes made of such resins are liable to stick to one another due to blocking.

Until now, in order to avoid this problem, it has been necessary to array the medical instruments and tubes in good order in advance to the sterilizing operation, or to take the trouble of separating the sticking instruments and tubes after the sterilization. Such procedures are quite troublesome and require much labor and, hence, there is an increasing demand for a technique which can eliminate the necessity for such operations.

SUMMARY OF THE INVENTION

Accordingly, it is a primary object of the invention to provide a tube for medical instruments, made of a material having a tendency for blocking and adapted to be connected to a medical instrument which is destined to be subjected to an autoclave sterilization, the tube being improved to eliminate any blocking during autoclave sterilization while exhibiting good bonding to another tube or to another instrument, as well as good characterics for hot stamping (printing) which may be conducted as required.

To this end, according to the invention, there is provided a tube for fluid connection with a medical instrument, made of a resin of vinylchloride group or ethylene-acetate group, the tube being of a material of the same kind as the medical instrument, wherein the improvement comprises a multiplicity of projections such as ribs extending substantially in the axial direction on the outer peripheral surface of the tube, the cross-section along its each rib having a length of bottom side ranging between 0.15 and 0.26 mm and a height ranging between 0.007 and 0.04 mm as measured from the bottom side to the top side thereof.

Taking productivity into account, the tube of the invention having external ribs is preferably produced by extrusion. The ribs may be formed in the form of straight lines or in spiral lines. It is noted that the term blocking means a sticking phenomenon among contact portions of materials.

BRIEF DESCRIPTION OF THE DRAWINGS

FIG. 1a is a front elevational view of a tube for a medical instrument having straight rib lines, in accordance with an embodiment of the invention;

FIG. 1b is an end view of the tube as shown in FIG. 1;

FIG. 2a is a enlarged sectional view of ribs in the portion encircled by a circle in FIG. 1b;

FIGS. 2b and 2c are enlarged sectional views of ribs the cross-sections of which are semi-circular and trapezoidal, respectively;

DESCRIPTION OF THE PREFERRED EMBODIMENTS

The tube for medical instruments, in accordance with a preferred embodiment of the invention, will be described hereinunder with reference to the accompanying drawings.

Conventional tubes made of a material having a tendency of blocking, such as a resin of vinylchloride group, EVA resin or the like, have been produced by extrusion to have a smooth outer peripheral surface. Due to the smooth nature of the tube surfaces, the tubes exhibited a heavy tendency of blocking or adhesive characteristic when they are stacked during autoclave sterlization.

Figure 3:
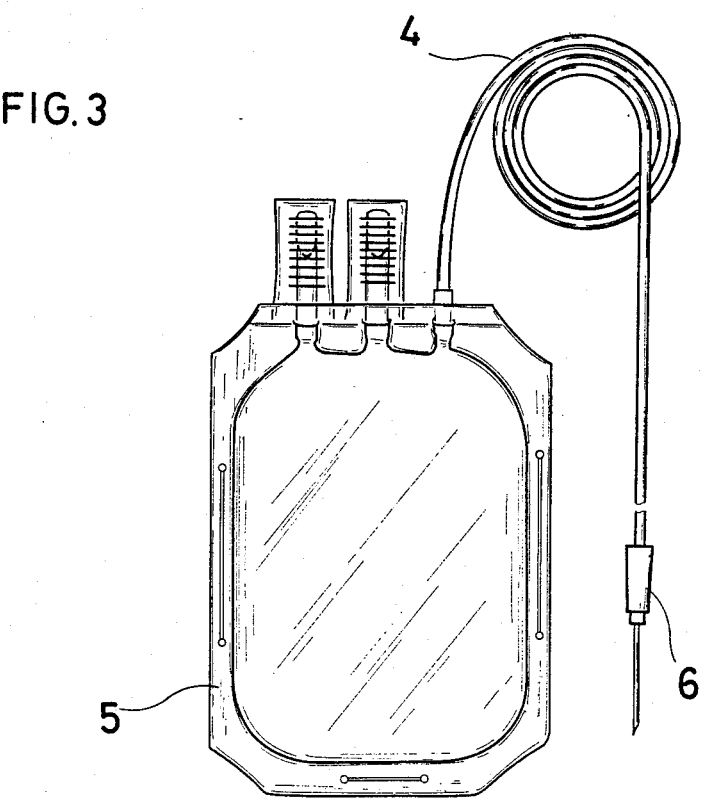
FIG. 3 shows a medical bag device with a tube of the present invention.
Figure 4:
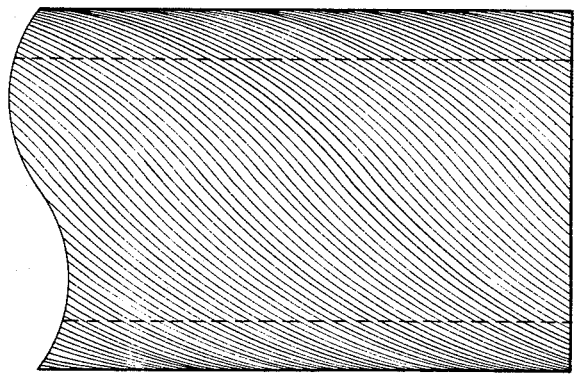
FIG. 4 is a front elevational view of a tube having spiral rib lines.

Under this circumstance, the present invention aims at eliminating the above-described problem of the conventional tube by providing substantially all the outer peripheral surface of the tube 1 with a multiplicity of straight ribs 2 as shown in FIG. 1 or of spiral ribs as shown in FIG. 4. In the present invention, the ribs may include projections whose cross-section is triangle, semi-circle, trapezoid or the like configurations. A tube for use in combination with a medical instrument is required to have the following characteristics, in addition to the anti-blocking nature mentioned above. Namely, considering that the tube is connected to another medical instrument or another tube, the tube should be able to be connected to such instrument or tube in an easy and good manner. The tube is also required to permit an easy hot stamping for a printing identification mark or the like thereon.

It has been discovered that, in order to cope with these demands, the ribs formed on the tube of the invention should meet the following conditions. Namely, each of the ribs 2 formed on the tube 1 has, for example, a substantially triangular cross-section as shown in FIG. 2a, with a bottom or base side (a) of a lenth ranging between 0.15 and 0.26 mm and a height (h) ranging between 0.007 and 0.04 mm. Any triangular form meeting the above-mentioned ranges of length of bottom side (a) and height (h) is acceptable. Namely, the lengths of legs of the triangle may be equal to or different from each other. The triangle may be an acute or obtuse one.

According to the invention, the above-mentioned restriction of the form of the ribs is imposed in view of the results of various performance tests conducted with various values of the rib height (h) and rib breadth (a) using a vinylchloride resin tube having an outside diameter of 4.4 mm and an inside diameter of 3.0 mm. The results of the tests are shown in Table 1 below.

(1) Anti-blocking characteristic

Conventional tubes having smooth surfaces and tubes of the invention were subjected to an autoclave sterilization, and the tendency of blocking was examined to confirm the anti-blocking characteristic of the tube of the invention. The estimation "good" on Table 1 includes the cases in which an extremely easy peeling may be performed even in case of blocking.

(2) Bonding characteristic

A check was made to confirm whether the connection between two tubes of the invention, as well as the connection of the tube of the invention to a Y-piece of the same kind of material, is deteriorated or not by the provision of the ribs.

(3) Hot-stamping characteristic

A check was made as to whether the tube of the invention permits an easy and good hot-stamping (printing) which is effected conventionally on the tube of the kind described.

The anti-blocking characteristic and the hot-stamping characteristic are closely related to the height (h) and breadth (a) of the ribs formed on the outer peripheral surface of the tube. Namely, the rib height (h) and rib breadth (h) (See FIGS. 2a–2c) coming out of the above-mentioned ranges seriously deteriorate the anti-blocking characteristic, bonding characteristic and the hot-stamping characteristic of the tube, as will be clearly understood from Table 1. According to the invention, mutual sticking of tubes (blocking) takes place only at the area around the crests of the ribs 3 so that the area of blocking is much reduced as compared with the conventional tubes having smooth surfaces.

TABLE 1

| | | | bonding characteristics | | |
|---|---|---|---|---|---|
| rib height h ($\mu$m) | rib breadth a ($\mu$m) | hot-stamping characteristics | Y-piece connection | tube connection | blocking level |
| 2 | 700 | good | good | good | no difference from prior art |
| 5 | 620 | good | good | good | no difference from prior art |
| 7 | 150 | good | good | good | appreciable effect |
| 10–15 | 160 | good | good | good | appreciable effect |
| 20 | 200 | good | good | good | appreciable effect |
| 30 | 260 | good | good | good | appreciable effect |
| 40 | 260 | good | good | good | appreciable effect |
| 50–60 | 400 | not good | not good | not good | appreciable effect |
| 70 | 200 | not good | not good | not good | appreciable effect |
| 30 | 400 | good | good | good | no difference |
| 10–15 | 150 | good | good | good | from prior art appreciable effect |

For obtaining a higher productivity, the tube of the invention is produced preferably by extrusion. Considering that the ribs to be formed on the tube are minute, it is advisable to form the tube in two stages, namely a first stage in which the tube material is extruded from a die having larger size and, hence, having a greater size of grooves than the desired tube, and a second step in which the tube is elongated at a predetermined ratio of contraction. The ribs on the tube can have the form of straight lines or spiral lines, depending on the shape of the grooves in the die. It has been confirmed that an equal effect is obtainable regardless of whether the ribs are straight or spiral, provided that the cross-section of each rib meets the aforementiond conditions.

In the foregoing description of the embodiment, it is assumed that the tube has constant inside and outside diameters. Similar tests as those mentioned before were conducted while varying the inside and outside diameters of the tube. The test results showed that the performance is affected not by the number of ribs on the tube but acceptable performance is obtained provided that the shape and size of each rib fall within the ranges mentioned before. Thus, according to the invention, it is essential that each of a multiplicity of ribs formed on the tube has a cross-section which is, for example, triangular and has a breadth (length of bottom side) (a) and height (h) ranging between 0.15 and 0.26 mm and between 0.007 and 0.04 mm, respectively.

The triangular form of the rib is not exclusive, and a similar effect was obtained even with ribs having different cross-section shapes such as semi-circular cross-section as shown in FIG. 2b, trapezoidal cross-section as shown in FIG. 2c and so forth. Thus, all that is required is that the cross-section of each rib has a bottom side length and height which fall within respective ranges mentioned above.

As will be understood from the foregoing description, the tube for medical instruments of the invention provided with ribs offers the following advantages over the conventional tubes having smooth surfaces.

(1) It is not necessary to take the trouble of arraying tubes in good order in advance to an autoclave sterilization, for avoiding blocking during the autoclave sterilization.

(2) The tubes of the invention have an extremely small tendency for blocking if they are subjected to an autoclave sterilization in a stacked manner. Even if any blocking takes place during the autoclave sterilization, the tubes can be separated quite easily because the sticking takes place only in the area around the crests of the ribs.

(3) After extraction of blood by a blood transfusion set having a blood bag and a tube, the tube is knotted to prevent the reversing flow of the blood. According to the invention, it is possible to reduce the force required for knotting the tube, due to a smaller contact area among tube portions in companion to the conventional ones.

What I claim are:

1. A heat-sterilizable tube for fluid connection with a medical instrument made of resin of the kind which exhibits blocking or adhesive characteristics upon being subjected to an autoclave sterilization, comprising an elongated tube of the same kind of material as the medical instrument which material also exhibits said blocking or adhesive characteristics at elevated temperatures during said autoclave sterilization, said tube having a multiplicity of ribs extending substantially in the axial direction on the outer peripheral surface of said tube, said ribs being arranged around the periphery of said tube, said ribs each having a base side adjacent said tube and a crest radially outwardly of said tube, the cross-section of each rib having a length along the base side ranging between 0.15 and 0.26 mm, and a height ranging between 0.007 and 0.04 mm as measured from the base side to the crest of each of said ribs, whereby sticking together of mutually contacting portions of said ribbed tube during said autoclave sterilization is substantially prevented.

2. A tube according to claim 1, wherein said resin includes a selected one of vinylchloride group and ethylene-acetate group.

3. A tube according to claim 1, wherein each of said ribs has a substantially triangular cross-section, the base of said triangular ribs being radially inner relative to the crests thereof.

4. A tube according to claim 1, wherein each of said ribs has a substantially trapezoidal cross-section, the trapezoidal ribs having a radially inner base which is wider than radially outer crest portions thereof.

5. A tube according to claim 1, wherein each of said ribs has a base and a substantially arcuate cross-section portion, said base being radially inner relative to the arcuate portion.

6. A tube according to any one of claims 1 to 5, wherein said ribs are formed as straight lines parallel to the tube axis.

7. A tube according to any one of claims 1 to 5, wherein said ribs are formed as spiral lines relative to the tube axis.

8. A heat-sterilizable medical bag device, comprising:
a flexible bag for holding a medical solution therein and made of a resin which exhibits a blocking or adhesive characteristic under elevated temperatures corresponding to an autoclave sterilization, and
an elongated tube for fluid connection at one end thereof with said bag and also made of said resin which exhibits said blocking or adhesive characteristics at said elevated temperatures corresponding to an autoclave sterilization,
said tube having a multiplicity of ribs extending substantially in the axial direction on the outer peripheral surface of said tube, said ribs being arranged around the periphery of said tube, said ribs each having a base side adjacent said tube and a crest radially outwardly of said tube, the cross-section of each rib having a length along the base side ranging between 0.15 and 0.26 mm, and a height ranging between 0.007 and 0.04 mm as measured from the base side to the crest of each of said ribs, whereby sticking together of mutually contacting portions of said ribbed tube during said autoclave sterilization is substantially prevented.

9. A device according to claim 8, wherein said resin a selected one of vinylchloride group and ethylene-acetate group.

10. A device according to claim 8, wherein each of said ribs has a substantially triangular cross-section, the base of said triangular ribs being radially inner relative to the crests thereof.

11. A device according to claim 8, wherein each of said ribs has a substantially trapezoidal cross-section, the trapezoidal ribs having a radially inner base which is wider than radially outer crest portions thereof.

12. A device according to claim 8, wherein each of said ribs has a base and a substantially arcuate cross-section, said base being radially inner relative to the arcuate portion.

13. A device according to any one of claims 8 to 12, wherein said ribs are formed as straight lines parallel to the tube axis.

14. A device according to any one of claims 8 to 12, wherein said ribs are formed as spiral lines parallel to the tube axis.

15. A device according to claim 8, wherein said flexible bag is arranged to hold a blood anti-coagulant solution.

16. A tube according to claim 1, wherein said elongated tube has an inside diameter of about 3.0 mm and an outside diameter of about 4.4 mm.

17. A device according to claim 8, wherein said elongated tube has an inside diameter of about 3.0 mm and an outside diameter of about 4.4 mm.

18. A tube according to claim 1, wherein said tube is subjected to autoclave sterilization.

19. A tube according to claim 1, comprising indicia printed on said ribbed outer peripheral surface of said tube.

20. A device according to claim 8, wherein said tube is subjected to autoclave sterilization.

21. A device according to claim 8, comprising indicia printed on said ribbed outer peripheral surface of said tube.

* * * * *

UNITED STATES PATENT AND TRADEMARK OFFICE
CERTIFICATE OF CORRECTION

PATENT NO. : 4,551,140

DATED : November 5, 1985

INVENTOR(S) : Shuichi SHINOHARA

It is certified that error appears in the above-identified patent and that said Letters Patent is hereby corrected as shown below:

COLUMN 6 (claim 9), line 16, change "resin a" to --resin includes a--.

Signed and Sealed this

Sixth Day of May 1986

[SEAL]

Attest:

Attesting Officer

DONALD J. QUIGG

Commissioner of Patents and Trademarks

UNITED STATES PATENT AND TRADEMARK OFFICE
CERTIFICATE OF CORRECTION

PATENT NO. : 4,551,140
DATED : November 5, 1985
INVENTOR(S) : Shuichi SHINOHARA

It is certified that error appears in the above-identified patent and that said Letters Patent is hereby corrected as shown below:

Column 1, line 67, change "along its rib having a length of bottom side" to --of each rib having a length along its bottom side--.

Signed and Sealed this

Seventh Day of October, 1986

[SEAL]

*Attest:*

DONALD J. QUIGG

*Attesting Officer*  *Commissioner of Patents and Trademarks*